(12) United States Patent
Bachan et al.

(10) Patent No.: US 9,205,218 B1
(45) Date of Patent: Dec. 8, 2015

(54) WEARABLE AIR PURIFIER ASSEMBLY

(71) Applicants: Nardeo Bachan, Ancaster (CA); Vashti Bachan, Ancaster (CA)

(72) Inventors: Nardeo Bachan, Ancaster (CA); Vashti Bachan, Ancaster (CA)

(*) Notice: Subject to any disclaimer, the term of this patent is extended or adjusted under 35 U.S.C. 154(b) by 12 days.

(21) Appl. No.: 14/158,908

(22) Filed: Jan. 20, 2014

(51) Int. Cl.
*A61M 16/00* (2006.01)
*A61M 16/10* (2006.01)

(52) U.S. Cl.
CPC .................... *A61M 16/105* (2013.01)

(58) Field of Classification Search
CPC ........... B01D 53/261; B01D 2253/102; B01D 2253/108; B01D 2253/25; B01D 2257/106; B01D 2257/302; B01D 2257/702; B01D 2257/80; B01D 2257/90; B01D 2257/91; B01D 2259/4533; B01D 2259/4541; B01D 2259/4583; Y10S 55/33; Y10S 55/35
USPC ........ 55/385.1, DIG. 35; 96/224; 128/202.22, 128/205.27, 206.12
See application file for complete search history.

(56) References Cited

U.S. PATENT DOCUMENTS

| 5,165,395 | A | * | 11/1992 | Ricci ..................... 128/202.22 |
| 5,564,124 | A | | 10/1996 | Elsherif et al. |
| 5,667,564 | A | * | 9/1997 | Weinberg ..................... 96/58 |
| 5,861,127 | A | | 1/1999 | Yeh |
| 6,135,714 | A | | 10/2000 | Hsu |
| D464,420 | S | | 10/2002 | Tolar |
| 8,333,816 | B2 | | 12/2012 | Kummer et al. |
| 2005/0223902 | A1 | * | 10/2005 | Lovell ..................... 96/134 |
| 2007/0257383 | A1 | | 11/2007 | Chan |
| 2008/0307970 | A1 | | 12/2008 | Augustine et al. |
| 2010/0108071 | A1 | | 5/2010 | Macy, Jr. |
| 2011/0126828 | A1 | | 6/2011 | Wu et al. |

* cited by examiner

*Primary Examiner* — Duane Smith
*Assistant Examiner* — Minh-Chau Pham

(57) ABSTRACT

A wearable air purifier assembly provides filtered air that is directed toward a person's nose and mouth. The assembly includes a housing. A tether is constructed of a flexible material and is attached to the housing. The tether is configured to be positioned around a person's neck to suspend the housing from the person's neck. A filter is positioned within the interior space of the housing for filtering the ambient air drawn into the interior space of the housing. An output fan is coupled to the housing and positioned proximate a second end of the housing. The output fan is in fluid communication with the ambient air filtered by the filter wherein the output fan directs the ambient air filtered by the filter outwardly of the housing toward a nose and mouth of the person wearing the assembly.

19 Claims, 3 Drawing Sheets

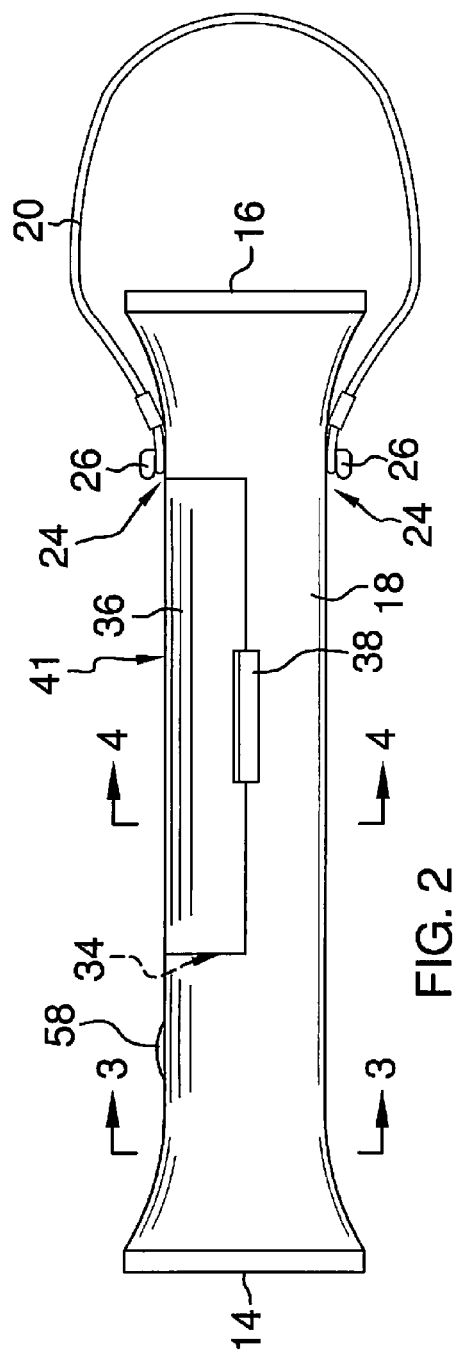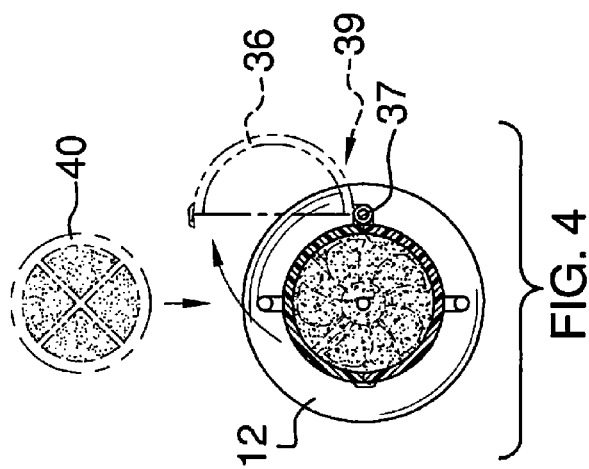
FIG. 2
FIG. 3
FIG. 4

WEARABLE AIR PURIFIER ASSEMBLY

BACKGROUND OF THE DISCLOSURE

Field of the Disclosure

The disclosure relates to air purifier assemblies and more particularly pertains to a new air purifier assembly for providing filtered air that is directed toward a person's nose and mouth.

SUMMARY OF THE DISCLOSURE

An embodiment of the disclosure meets the needs presented above by generally comprising a housing. A tether is comprised of a flexible material and is attached to the housing. The tether is configured to be positioned around a person's neck to suspend the housing from the person's neck. A filter is positioned within the interior space of the housing for filtering the ambient air drawn into the interior space of the housing. An output fan is coupled to the housing and positioned proximate a second end of the housing. The output fan is in fluid communication with the ambient air filtered by the filter wherein the output fan directs the ambient air filtered by the filter outwardly of the housing toward a nose and mouth of the person wearing the assembly.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 2 is a side view of an embodiment of the disclosure.

FIG. 3 is a cut-away view of an embodiment of the disclosure taken along line 3-3 of FIG. 2.

FIG. 4 is a cut-away view of an embodiment of the disclosure taken along line 4-4 of FIG. 2.

DESCRIPTION OF THE PREFERRED EMBODIMENT

Figure 1:
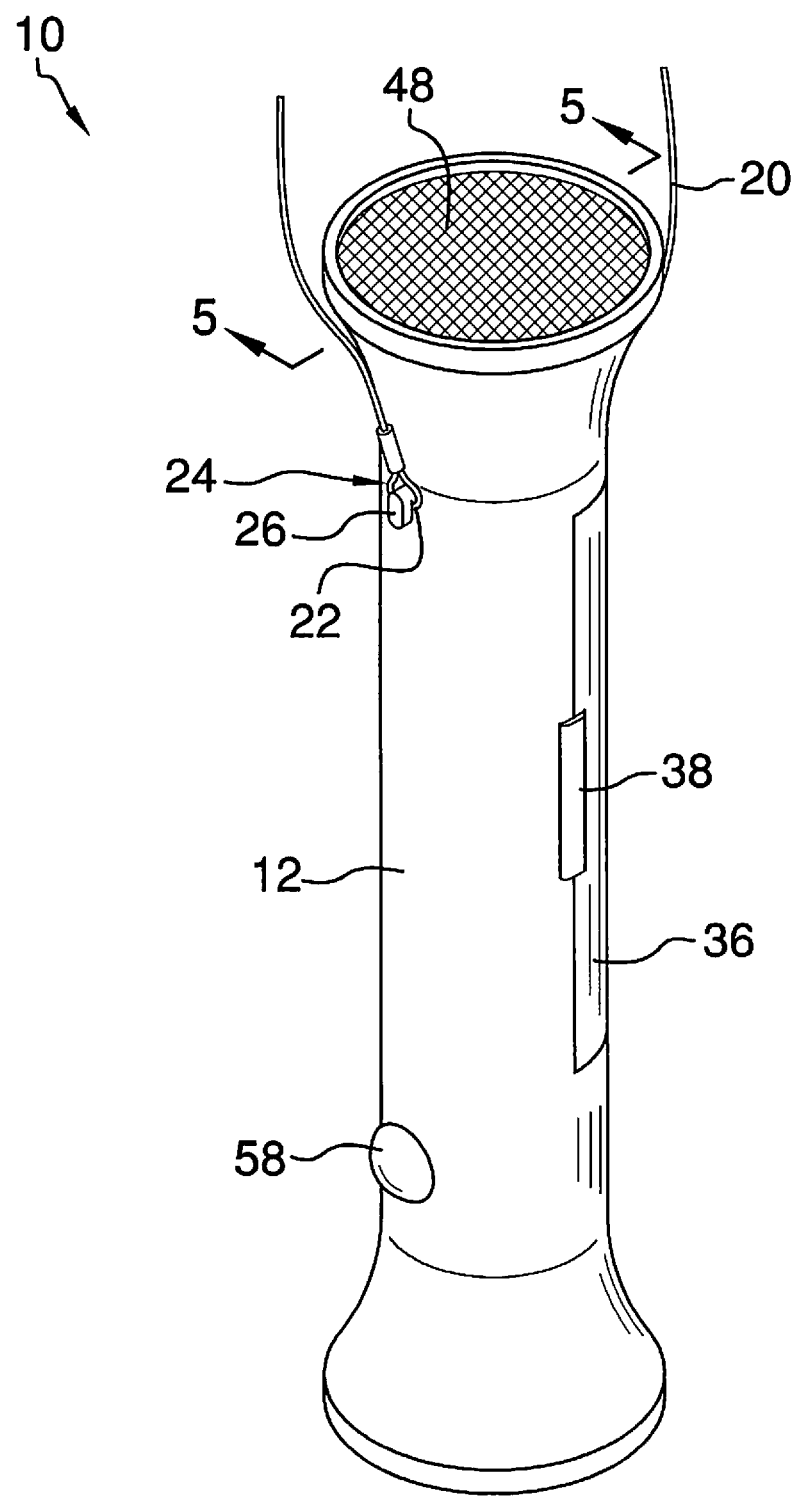
FIG. 1 is a top front side perspective view of a wearable air purifier assembly according to an embodiment of the disclosure.
Figure 5:
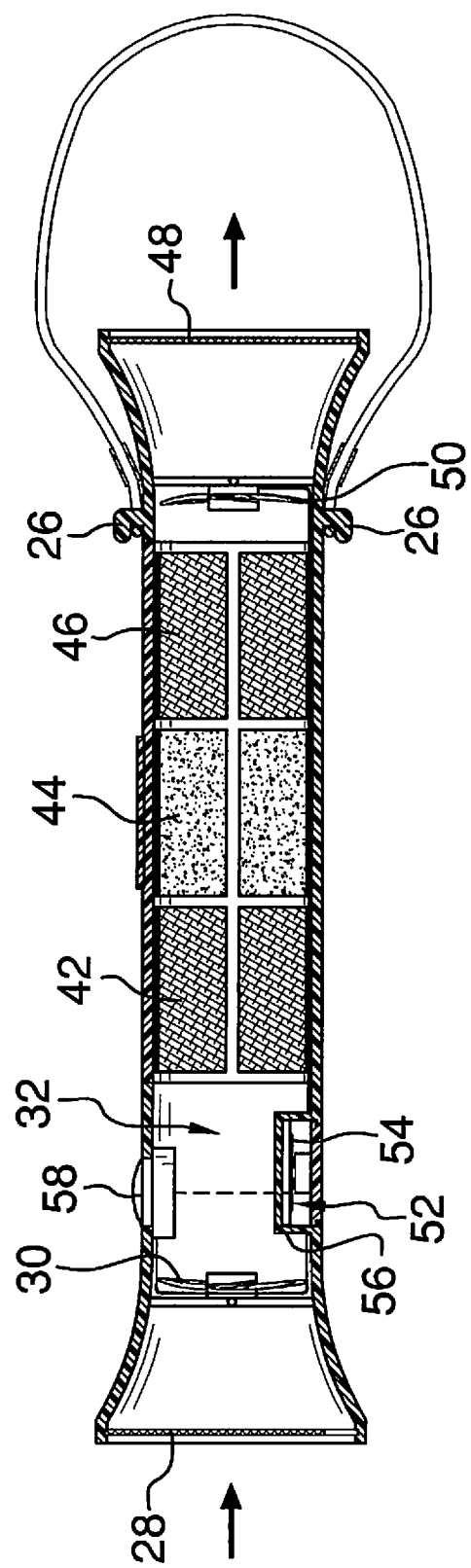
FIG. 5 is a cross-sectional view of an embodiment of the disclosure taken along line 5-5 of FIG. 1.

With reference now to the drawings, and in particular to FIGS. 1 through 5 thereof, a new air purifier assembly embodying the principles and concepts of an embodiment of the disclosure and generally designated by the reference numeral 10 will be described.

As best illustrated in FIGS. 1 through 5, the wearable air purifier assembly 10 generally comprises a housing 12 having a first end 14, a second end 16 and a perimeter surface 18 coupled to and extending between the first end 14 and the second end 16. The perimeter surface 18 tapers outwardly toward each of the first end 14 and the second end 16. The housing 12 is constructed from a lightweight material, such as plastic or the like to facilitate portability of the assembly 10. The housing 12 may have a length between approximately 10.0 centimeters and 30.0 centimeters and a diameter between approximately 2.5 centimeters and 9.0 centimeters.

A tether 20 is comprised of a flexible material. The tether 20 is attached to the housing 12. The tether 20 is configured to be positioned around a person's neck to suspend the housing 12 from the person's neck. Each of a pair of outer ends 22 of the tether 20 is formed into an associated loop 24. A pair of hooks 26 is coupled to the housing 12. Each of the hooks 26 is selectively engageable with an associated one of the loops 24 for releasably coupling the tether 20 to the housing 12.

A first screen 28 is coupled to the first end 14 of the housing 12 whereby the first screen 28 is in fluid communication with ambient air space surrounding the first screen 28. An intake fan 30 is coupled to the housing 12 and is positioned proximate the first end 14 of the housing 12. The intake fan 30 may be positioned within an interior space 32 of the housing 12. The intake fan 30 is in fluid communication with the ambient air space surrounding the first screen 28 wherein the intake fan 30 draws ambient air into the interior space 32 of the housing 12 through the first screen 28.

An opening 34 is positioned in the housing 12. The opening 34 provides access to the interior space 32 of the housing 12. A door 36 is coupled to the housing 12. The door 36 is positionable within the opening 34 to selectively cover the opening 34. A hinge 37 may couple the door 36 to the housing 12 to allow the door 36 to pivot between an opened position 39 exposing the opening 34 and a closed position 41 covering the opening 34. A closure 38 is coupled to the door 36. The closure 38 is selectively engageable with the housing 12 wherein the closure 38 is configured to retain the door 36 in the closed position 41. The closure 38 may comprise a latch or other similar type of closure.

A plurality of filters 40 is provided. Each of the filters 40 is positionable within the interior space 32 of the housing 12 for filtering the ambient air drawn into the interior space 32 of the housing 12. The filters 40 are generally conventional and may include a first filter 42, a second filter 44 and a third filter 46. The first filter 42 and the third filter 46 may be constructed from foam, while the second filter 44 may be a carbon filter. Each of the first filter 42, the second filter 44 and the third filter 46 is positionable adjacent to each other within the interior space 32 of the housing 12. The intake fan 30 is spaced from each of the filters 40. The filters 40 may include fragrances such that the ambient air filtered by the filters 40 and directed outwardly of the housing 12 is scented.

A second screen 48 is coupled to the second end 16 of the housing 12 whereby the second screen 48 is in fluid communication with ambient air space surrounding the second screen 48. An output fan 50 is coupled to the housing 12 and is positioned proximate the second end 16 of the housing 12. The output fan 50 may also be positioned within the interior space 32 of the housing 12. The output fan 50 is in fluid communication with the ambient air filtered by the filters 40 wherein the output fan 50 directs the ambient air filtered by the filters 40 outwardly of the housing 12 through the second screen 48 toward a nose and mouth of the person wearing the assembly 10. The output fan 50 is spaced from each of the filters 40.

A power source 52 is coupled to the housing 12. The power source 52 is electrically coupled to the intake fan 30 and the output fan 50 for providing power to the intake fan 30 and the output fan 50. The power source 52 may comprise a battery 54 positioned within a compartment 56 of the housing 12. An on/off switch 58 is coupled to the housing 12. The on/off switch 58 is electrically coupled to the power source 52 for selectively turning the intake fan 30 and the output fan 50 on and off.

In use, as stated above and shown in the Figures, the tether 20 is positioned around a person's neck. The on/off switch 58 is manipulated to turn the intake fan 30 and the output fan 50 on. The intake fan 30 draws ambient air in through the first screen 28. The filters 40 filter the ambient air as it passes through the filters 40. The output fan 50 directs the filtered air outwardly through the second screen 48 and toward a nose and mouth of the person wearing the assembly 10. After use, the on/off switch 58 is again manipulated to turn off the intake fan 30 and the output fan 50. The assembly 10 can continue to be worn around the user's neck or can be stored until needed again.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

We claim:

1. A wearable air purifier assembly comprising:
   a housing having a first end, a second end and a perimeter surface coupled to and extending between said first end and said second end, said housing being elongated and tubular extending between said first end and said second end;
   a tether being comprised of a flexible material, said tether being attached to said housing such that said tether extends from said second end of said housing wherein said tether is configured to be positioned around a person's neck to suspend said housing from the person's neck such that said second end of said housing is directed upwardly facing a face of the person;
   a filter positioned within said interior space of said housing for filtering the ambient air drawn into said interior space of said housing; and
   an output fan coupled to said housing and being positioned proximate said second end of said housing, said output fan being in fluid communication with the ambient air filtered by said filter wherein said output fan directs the ambient air filtered by said filter outwardly of said housing through said second end of said housing toward a nose and mouth of the person wearing said assembly.

2. The assembly of claim 1, further comprising said perimeter surface tapering outwardly toward each of said first end and said second end of said housing.

3. The assembly of claim 1, further comprising:
   each of a pair of outer ends of said tether being formed into an associated loop; and
   a pair of hooks coupled to said housing, each of said hooks being selectively engageable with an associated one of said loops for releasably coupling said tether to said housing.

4. The assembly of claim 1, further comprising:
   an opening positioned in said housing, said opening providing access to said interior space of said housing; and
   a door coupled to said housing, said door being positionable within said opening to selectively cover said opening.

5. The assembly of claim 4, further comprising a closure coupled to said door, said closure being selectively engageable with said housing wherein said closure is configured to retain said door in a closed position covering said opening.

6. The assembly of claim 1, further comprising a first screen coupled to said first end of said housing whereby said first screen is in fluid communication with ambient air space surrounding said first screen.

7. The assembly of claim 6, further comprising a second screen coupled to said second end of said housing whereby said second screen is in fluid communication with ambient air space surrounding said second screen.

8. The assembly of claim 6, further comprising an intake fan coupled to said housing and being positioned proximate said first end of said housing, said intake fan being in fluid communication with the ambient air space surrounding said first screen wherein said intake fan draws ambient air into said interior space of said housing through said first screen.

9. The assembly of claim 8, further comprising said intake fan being positioned within said interior space of said housing.

10. The assembly of claim 1, further comprising said filter being removably positionable within said interior space of said housing.

11. The assembly of claim 8, further comprising said intake fan being spaced from said filter.

12. The assembly of claim 1, further comprising said filter being one of a plurality of said filters, each of said filters being positioned adjacent to each other within said interior space of said housing.

13. The assembly of claim 1, further comprising said output fan being positioned within said interior space of said housing.

14. The assembly of claim 1, further comprising said output fan being spaced from said filter.

15. The assembly of claim 8, further comprising a power source coupled to said housing, said power source being electrically coupled to said intake fan and said output fan for providing power to said intake fan and said output fan.

16. The assembly of claim 15, further comprising said power source comprising a battery positioned within a compartment of said housing.

17. The assembly of claim 15, further comprising an on/off switch coupled to said housing, said on/off switch being electrically coupled to said power source for selectively turning said intake fan and said output fan on and off.

18. The assembly of claim 4, further comprising a hinge coupling said door to said housing to allow said door to pivot between an opened position exposing said opening and a closed position covering said opening.

19. A wearable air purifier assembly comprising:
   a housing having a first end, a second end and a perimeter surface coupled to and extending between said first end and said second end, said perimeter surface tapering outwardly toward said first end and toward said second end, said housing being elongated and tubular extending between said first end and said second end;

a tether being comprised of a flexible material, said tether being attached to said housing such that said tether extends from said second end of said housing wherein said tether is configured to be positioned around a person's neck to suspend said housing from the person's neck such that said second end of said housing is directed upwardly facing a face of the person, each of a pair of outer ends of said tether being formed into an associated loop;

a pair of hooks coupled to said housing, each of said hooks being selectively engageable with an associated one of said loops for releasably coupling said tether to said housing;

an opening positioned in said housing, said opening providing access to said interior space of said housing;

a door coupled to said housing, said door being positionable within said opening to selectively cover said opening;

a hinge coupling said door to said housing to allow said door to pivot between an opened position exposing said opening and a closed position covering said opening;

a closure coupled to said door, said closure being selectively engageable with said housing wherein said closure is configured to retain said door in the closed position, said closure comprising a latch;

a first screen coupled to said first end of said housing whereby said first screen is in fluid communication with ambient air space surrounding said first screen;

a second screen coupled to said second end of said housing whereby said second screen is in fluid communication with ambient air space surrounding said second screen;

an intake fan coupled to said housing and being positioned proximate said first end of said housing, said intake fan being positioned within said interior space of said housing, said intake fan being in fluid communication with the ambient air space surrounding said first screen wherein said intake fan draws ambient air into said interior space of said housing through said first screen;

a plurality of filters, each of said filters being positionable within said interior space of said housing for filtering the ambient air drawn into said interior space of said housing, said plurality of filters comprising a first filter, a second filter and a third filter, each of said first filter, said second filter and said third filter being positionable adjacent to each other within said interior space of said housing, said intake fan being spaced from each of said filters;

an output fan coupled to said housing and being positioned proximate said second end of said housing, said output fan being positioned within said interior space of said housing, said output fan being in fluid communication with the ambient air filtered by said filters wherein said output fan directs the ambient air filtered by said filters outwardly of said housing through said second screen toward a nose and mouth of the person wearing said assembly, said output fan being spaced from said each of said filters;

a power source coupled to said housing, said power source being electrically coupled to said intake fan and said output fan for providing power to said intake fan and said output fan, said power source comprising a battery positioned within a compartment of said housing; and an on/off switch coupled to said housing, said on/off switch being electrically coupled to said power source for selectively turning said intake fan and said output fan on and off.

\* \* \* \* \*